United States Patent [19]

Nishihara

[11] Patent Number: 5,219,287
[45] Date of Patent: Jun. 15, 1993

[54] ARTIFICIAL DENTAL ROOT HAVING FUNCTION OF NATURAL DENTAL ROOT

[75] Inventor: Katsunari Nishihara, Tokyo, Japan

[73] Assignees: Katsunari Nishihara; Toyama Precious Metals Co., Ltd., both of Tokyo, Japan

[21] Appl. No.: 816,374

[22] Filed: Dec. 30, 1991

[30] Foreign Application Priority Data

May 23, 1991 [JP] Japan ................................ 3-118604

[51] Int. Cl.$^5$ .............................................. A61C 8/00
[52] U.S. Cl. .................. 433/201.1; 433/173; 433/175
[58] Field of Search ............. 433/173, 175, 176, 201.1

[56] References Cited

U.S. PATENT DOCUMENTS 4,468,201  8/1984  Fukuyo ............................... 433/176
4,865,663  9/1989  Tuominen et al. ................. 148/402

FOREIGN PATENT DOCUMENTS 1-113060  5/1989  Japan .

Primary Examiner—John J. Wilson
Attorney, Agent, or Firm—Flynn, Thiel, Boutell & Tanis

[57] ABSTRACT

An artificial dental root having the function of a natural dental root is characterized in that the artificial dental root is made a shape-memorizing alloy capable of changing the apex morphology of the artificial dental root after implantation so as to stay in the jawbone. The artificial dental root is implanted in an alveolus and the apexes thereof then closely contact the inner surface of the alveolus owing to the shape-memorizing effect thereof to fix the dental root firmly in the alveolus.

1 Claim, 1 Drawing Sheet

ARTIFICIAL DENTAL ROOT HAVING FUNCTION OF NATURAL DENTAL ROOT

BACKGROUND OF THE INVENTION

1. Field of the Invention

The present invention relates to an improvement in an artificial dental root.

2. Description of the Prior Art

Recently, dental implants have been in practical use in place of removable dentures. However, the method joining implants to the jawbone has involved unsolved problems. Infections and absorption of alveolar bone have become serious issues.

The concept of an artificial root is quite different from that of a dental implant. A dental implant has no effective root-supporting tissue necessary for mastication. In contrast thereto an artificial root has a root-supporting apparatus effective for masticatory functions. The inventor developed a hydroxyapatite artificial root of the fibrous tissue attachment type. This artificial root is joined to the jawbone by a method resembling ligamentous gomphosis of the natural tooth. However, the artificial root has been very unstable immediately after the operation and, therefor, very easily falls out.

SUMMARY OF THE INVENTION

The present invention is directed to a functional artificial root made a shape-memorizing alloy, of which the apex morphology changes due to a lowering of its temperature after implantation so as to stay in the jawbone.

This artificial root joint system resembles that of the natural tooth and has ligamentous periodontal fibrous tissues attaching to alveolar bone. Ligamentous fibrous tissues have functional orientation, which on one side attach to the artificial root surface and on the other side of the alveolar bone.

This newly invented artificial root functions to prevent the absorption of alveolar bone. Falling out of the artificial root can be prevented by changing the root-shape in this newly invented artificial root made of a shape-memorizing alloy.

DETAILED DESCRIPTION OF THE PREFERRED EMBODIMENTS

A shape-memorizing alloy having characteristics that do not adversely affect a human body is used. For example, a TiPd alloy and a TiPd-Co alloy in which a part of Pd is substituted by Co are preferably used.

When an artificial dental root according to the present invention is implanted in a jawbone, the apex thereof returns to its original shape by body heat and the apex morphology changes, whereby the apexes are fixed in close contact with the inner surface of an alveolus formed in a jawbone, so that the fall-off of the artificial dental root is prevented.

Figure 1:
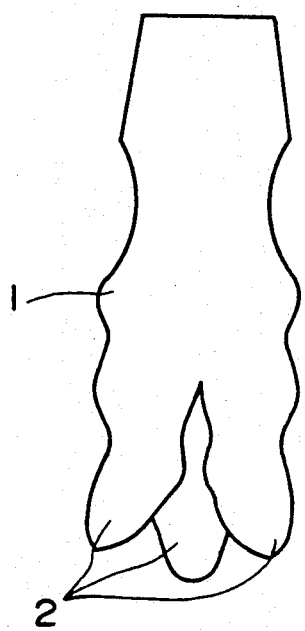
FIG. 1 is a front elevation of an embodiment of the molar of the present invention.
Figure 2:
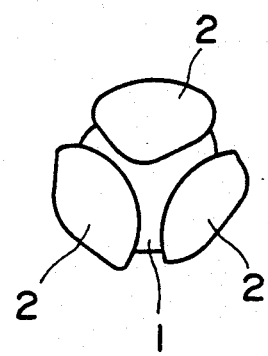
FIG. 2 is a bottom view of the embodiment of the molar.
Figure 3:
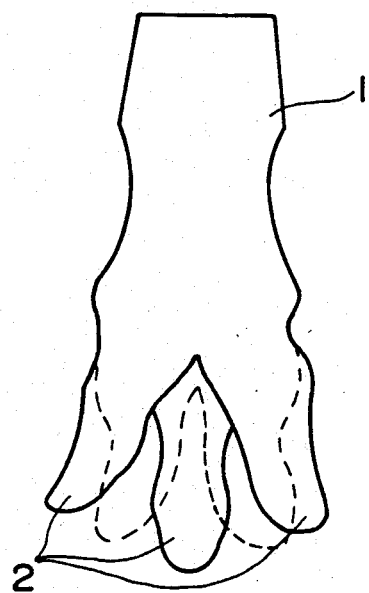
FIG. 3 is an illustration of the function of the embodiment of the molar.

An embodiment will now be described with reference to the drawings FIG. 1 is a front elevation of an embodiment and FIG. 2 a bottom view thereof. A reference numeral 1 denotes an artificial dental root body having three root members 2 at the lower portion thereof in the same manner as a natural upper molar. The dental root body as a whole is formed out of a shape-memorizing alloy consisting of TiPd-Co. A bore is made as an alveolus in a jawbone, and the artificial root members 2 are buried upright therein up to the neck portions thereof to have the root members reach a transformation temperature. Consequently, the branching root members 2 are opened from their deformed positions shown by a broken line to the positions shown by a solid line in FIG. 3, in compliance with an original shape set in advance. The apexes of the branching root member 2 then firmly contact the inner surface of the alveolus in the jawbone and are fixed thereto, so that there is no possibility of their coming off from the alveolus. In this embodiment, the dental root has three root members 2 consisting of three branching apexes thereof. An artificial lower molar and an artificial upper premolar each have two root members, and an artificial lower premolar, artificial upper and lower front teeth and artificial canines each have one root member, and the apexes of these artificial teeth consist of a shape-memorizing alloy bent centrifugally in the same manner as the corresponding natural teeth.

According to the present invention, an operation for implanting an artificial dental root in a jawbone is carried out, and the apexes of this dental root then closely contact the inner surface of an alveolus in a jawbone owing to the shape-memorizing effect thereof, whereby the apexes are firmly fixed. These apexes are then joined ligamentously with the jawbone with fibrous tissue in accordance with the function thereof in the same manner as a natural tooth, so that there is no possibility of their coming off from the alveolus.

What is claimed is:

1. An artificial dental root having the function of a natural dental root, said artificial dental root being made of a shape-memorizing alloy capable of changing the artificial dental root's apex morphology after implantation by body heat so that said artificial dental root joins ligamentously with the jawbone with fibrous tissue in the same manner as a natural tooth, said alloy being selected from the group of nickel free alloy consisting of a TiPd alloy and a TiPd-Co alloy.

* * * * *